United States Patent [19]

Teffenhart

[11] Patent Number: 4,789,720

[45] Date of Patent: Dec. 6, 1988

[54] HYDROPHILIC POLYURETHANES PREPARED FROM MIXED OXYALKYLENE GLYCOLS

[75] Inventor: John M. Teffenhart, Neshanic Station, N.J.

[73] Assignee: Tyndale Plains-Hunter, Ltd., Princeton, N.J.

[21] Appl. No.: 166,091

[22] Filed: Mar. 9, 1988

[51] Int. Cl.$^4$ ............................................. C08G 18/48
[52] U.S. Cl. ....................................... 528/76; 528/904
[58] Field of Search ................................... 528/76, 904

[56] References Cited

U.S. PATENT DOCUMENTS 3,822,238   7/1974   Blair et al. .............................. 528/59
3,975,350   8/1976   Hudgin .................................. 528/293

Primary Examiner—Maurice J. Welsh
Attorney, Agent, or Firm—Ratner & Prestia

[57] ABSTRACT

A hydrophilic, thermoplastic polyurethane polymer of improved dimensional stability and mechanical strength having an average molecular weight of from about 10,000 to about 200,000 produced by reacting (A) an organic diisocyanate with (B) a blend of glycol components comprising (i) ethylene glycol and/or diethylene glycol, (ii) a polyoxyethylene glycol having an average molecular weight of from about 400 to about 20,000 and (iii) a polyoxypropylene glycol having an average molecular weight of from about 200 to about 2500, and (C) water in an amount up to about 0.5% by weight of the reaction mixture. The polymers are particularly useful in the form of a film product such as gloves and condoms. Other uses are as low friction coatings, body implants and active agent release media.

45 Claims, No Drawings

HYDROPHILIC POLYURETHANES PREPARED FROM MIXED OXYALKYLENE GLYCOLS

TECHNICAL FIELD

This invention relates to polyurethane polymers, and in particular to hydrophilic polyurethane polymers prepared from a combination of certain alkylene glycols and to coatings, films, carrier systems and various articles based on the polymers.

BACKGROUND OF THE INVENTION

U.S. Pat. Nos. 3,822,238 and 3,975,350 describe a class of hydrophilic polyurethane polymers which, on contact with an aqueous medium, absorb water with concomitant formation of a stable, water-insoluble hydrogel. In the water swelled state, the polyurethane polymers of the cited patents vary from gel-like to soft and pliable and in the dry state from soft to hard and machinable. Suggested uses are as coatings, linings, dialysis membranes, absorbents, controlled release agents, swellable fabrics, gauzes, solubilizing packaging components, water transmitting coated fabrics, water swelling caulks, wet friction elastomers, artificial leather, gas filters, dentures, hair sprays, nail polishes and oil resistant shapes.

One type of the hydrophilic polyurethanes aforesaid, and one with which the present invention is particularly concerned, is produced by reacting (A) a diol component comprising a water soluble polyoxyethylene glycol having an average molecular weight of from about 400 to about 20,000 and an alkylene glycol selected from the class consisting of ethylene glycol and diethylene glycol, (B) a diisocyanate and (C) water in an amount constituting about 0.3% of the combined weight of the reactants, the ratio of NCO to OH in the diol being about 1:1 or slightly less than 1:1; and the weight ratio of the alkylene glycol to the polyoxyethylene glycol being from about 1:2 to about 1:10.

The resulting polymer is a hydroxy-terminated polyurethane consisting of polyoxyethylene units ($-OC_2H_4-$), so-called soft segments, and ethylene ($-C_2H_4-$) and/or diethylene ($-C_2H_4OC_2H_4-$) units, so-called hard segments, connected through urethane linkages. Also present in the polymer chain are urea segments which originate from the reaction of the water with isocyanate groups.

In these polymers, hydrophilicity is a function of the soft segments, i.e., the $-OC_2H_4-$ units derived from the polyoxyethylene glycol. Thus, to form a more hydrophilic polyurethane, the amount of and/or the molecular weight of the polyoxyethylene glycol reactant is increased to provide more soft segments in the polymer chain. Unfortunately, adding soft segments causes a progressive physical weakening of the polymer as manifested by decreasing tensile strength and tear resistance, particularly when the polymer is in the wet or swollen state.

On the other hand, increasing the hard segments, i.e., the $-C_2H_4-$ and/or $-C_2H_4OC_2H_4-$ units derived from the alkylene glycol, tends to increase the strength of the polymer. However, as more hard segments are introduced, the polymer becomes increasingly rigid and less hydrophilic, resulting in a diminished capacity to form hydrogels when immersed in aqueous media. Another deleterious side effect of adding hard segments is to decrease the solubility of the polymer in organic solvents, such as lower aliphatic alcohols of 1 to 5 carbon atoms, e.g., ethanol and isopropanol.

Nevertheless, by adjusting the proportions of soft and hard segments, it is possible, within limits, to counteract the unwanted side effects of the soft and hard segments, thereby providing polyurethanes that are a workable compromise of hydrophilic properties and mechanical strength.

DESCRIPTION OF THE INVENTION

It has now been found that the prior art hydrophilic polyurethanes can be further improved in physical properties without substantially diminishing their hydrophilicity by including as part of the diol component, a polyoxypropylene glycol. In formulating the reaction mixture, the OH equivalency of the total diol component is adjusted to give a ratio of NCO to OH in the range of about 0.95:1 to about 0.98:1. The reaction mixture will also contain some water but no more than about 0.5% by weight thereof.

Broadly speaking, the invention involves replacing a portion of the alkylene glycol and/or polyoxyethylene glycol used in preparing the prior art hydrophilic polyurethanes with a hydroxy equivalent of the polyoxypropylene glycol. Thus, given a representative prior art hydrophilic polyurethane having a certain percentage of hard and soft segments derived from ethylene or diethylene glycol and polyoxyethylene glycol, respectively, the physical properties of such polyurethane can be improved without substantial loss of hydrophilicity by replacing the alkylene glycol or polyoxyethylene glycol, preferably the latter, with an equivalent quantity of the polyoxypropylene glycol. The resulting polyurethane, as compared with the unmodified prior art polyurethane, exhibits improved tensile strength and tear resistance, both in the dry and wet state and is more pliant and soft as evidenced by a lower modulus.

So far as can be ascertained, the polyurethane polymers of the invention will overall fall within the average molecular weight range of from about 10,000 to 200,000.

The average molecular weight of the polyoxyethylene glycol reactant can vary from about 400 to about 20,000 while that of the polyoxypropylene glycol can range from about 200 to about 2500.

In preparing the hydrophilic polyurethanes of the invention, the amount of polyoxypropylene glycol included in the diol component can vary considerably, depending on the polymer properties desired. Generally speaking, the diol component will be a blend of (i) from about 2 to about 15 parts by weight of the lower alkylene glycol (hard segments), (ii) from about 10 to about 80 parts by weight of polyoxyethylene glycol (soft segments), and (iii) from about 10 to about 60 parts of the polyoxypropylene glycol. Each of the glycols i, ii and iii may be single glycols or a mixture of glycols differing in molecular weight. The sum of the diol component, diisocyanate and water in the reaction mixture will total 100 parts by weight.

The polyoxypropylene glycol, used in preparing the herein polyurethane polymer compositions, is a known chemical entity, the description and preparation of which can be found in the technical and patent literature. These glycols contain repeating isopropylene ether [$-OCH_2CH(CH_3)-$] groups and are commercially available from various sources, such as the PPG series of NIAX ® Polyether Polyols sold by Union Carbide Corporation. In the NIAX product designations the numbers refer to average molecular weight. Thus, NIAX® PPG 1025 polyoxypropylene glycol has an average molecular weight of 1025. Other useful NIAX Polyether Polyols include PPG-425, PPG-725, PPG-1225 and PPG-2025.

Polyoxyethylene glycols are available from Union Carbide Corporation under the trademark and designation CARBOWAX, such as CARBOWAX®1450 and CARBOWAX®8000, wherein the numbers represent average molecular weights.

The diisocyanates used in the present invention include both aliphatic and aromatic types and mixtures thereof although the aliphatics are preferred. Representative members are tetramethylene diisocyanate, hexamethylene diisocyanate, trimethylhexamethylene diisocyanate, dimer acid diisocyanate, isophorone diisocyanate, diethylbenzene diisocyanate, decamethylene 1,10-diisocyanate, cyclohexylene 1,2-diisocyanate and cyclohexylene 1,4-diisocyanate, and aromatic isocyanates such as 2,4- and 2,6-tolylene diisocyanate.

An especially preferred isocyanate is methylene bis(-cyclohexyl-4-isocyanate). Somewhat less preferred diisocyanates are trimethyl hexamethylene diisocyanate and isophorone diisocyanate.

Other compounds which are useful are the isocyanate equivalents which produce the urethane linkages such as nitrile carbonate, that is, the adiponitrile carbonate of the formula:

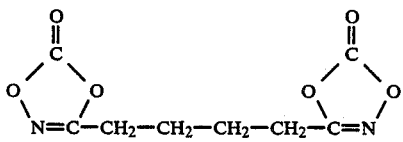

In making the polyurethane polymer of the invention, the glycol components are formed into a homogeneous mixture which is then reacted with the diisocyanate. The reaction is catalyzed by known catalysts for such reaction, suitable ones being tin salts and organic tin esters such as dibutyl tin dilaurate, tertiary amines such as triethylenediamine (DABCO), N,N,N',N'-tetramethyl-1,3-butane diamine and other recognized catalysts for urethane polymer synthesis.

The polymer of the invention absorbs water in aqueous media accompanied by varying degrees of swelling depending on the particular polymer composition. Water absorption is determined by immersing the polymer in water at 20° C. for 24 hours and weighing the polymer in the dry state and after removal from the water, and expressing the gain as % (by weight of polymer) of water absorbed.

The hydrophilic polyurethane polymer of the present invention are dimensionally stable upon repeated exposure to water and exhibits high mechanical strength, especially in the wet stage. These characteristics translate into superior film products made from the polymer such as, for example, condoms and gloves. Other uses include coatings, molding compounds, absorbents, carrier systems for active agents including a non-leachable carrier system, a leachable carrier system, and wherein the carrier system is disposed in liquid medium, e.g. a body fluid, or in a gaseous medium such as air, ion exchange resins, and such manufactured articles as dialysis membranes, dentures, cannulae, e.g. feeding tubes, contact lenses, packaging components, burn dressings, contraceptive devices, sutures, surgical implants, blood oxygenators, intrauterine devices, vascular prostheses, oral delivery systems, battery separator plates, eye bandages, corneal prostheses, antifog coatings, surgical drapes, oxygen exchange membranes, artificial fingernails, finger cots, adhesives, gas permeable membranes, and protective and drag resistant coatings.

The invention is further illustrated by the following examples, in which the components are in parts by weight unless stated otherwise.

POLYMER PREPARATION

Prior Art Hydrophilic Polyurethane A

A mixture of 57.4 parts of CARBOWAX 1450, 5.5 parts of ethylene glycol and 0.2 parts of water was heated to about 70° C. with stirring until a homogeneous melt was obtained. While continuing the stirring, 36.9 parts of methylene bis(cyclohexyl-4 isocyanate), a product sold as DESMODUR® W by the Mobay Chemical Corporation, were added during which the temperature decreased. When the temperature reached about 50° C., there was added 0.15 ml of stannous octoate, and the mass allowed to exotherm to about 70° C. The mass was then poured into a polypropylene pan. During pouring, the temperature continued to rise to about 80° C. and the mass foamed. Upon finishing of the pouring operation, the pan was placed in an oven and held at 100° C. for about one hour to complete formation of the polymer.

Prior Art Hydrophilic Polyurethane B 50.2 parts of CARBOWAX 1450 polyoxyethylene glycol was heated to melting after which it was blended with 10.7 parts of diethylene glycol and 0.3 parts of water. The resulting composition was heated to 60° C. and mixed with 38.8 Desmodur W diisocyanate preheated to the same temperature followed by the addition of 0.15 parts of stannous octoate. The mixture exothermed and was poured into a polypropylene tray and cured at 100° C. for 50 minutes.

Polymers Prepared With Polyoxypropylene Glycol

EXAMPLES 1-2

The foregoing procedure for preparing prior art hydrophilic polyurethane A was repeated except that NIAX®PPG 1025 polyoxypropylene glycol was included as part of the diol blend. This polyoxypropylene glycol has an average molecular weight of 1025 and is sold by Union Carbide Corporation. Two polymers of this type (Examples 1 and 2) were prepared differing in proportions of components. The polymer compositions and test data are set forth below:

TABLE 1

| | UNSUBSTITUTED PRIOR ART POLYMER A | SUBSTITUTED POLYMERS | |
|---|---|---|---|
| | | Example 1 | Example 2 |
| COMPOSITION - Parts by Weight | | | |
| CARBOWAX 1450 | 57.4 | 10.9 | 11.1 |
| CARBOWAX 1000 | | 7.5 | 7.7 |
| CARBOWAX 600 | | 4.5 | 4.6 |
| CARBOWAX 400 | | 3.0 | 3.1 |
| NIAX ® 1025 | | 19.7 | 23.2 |
| Ethylene glycol | 5.5 | 7.2 | 6.2 |
| Desmodur W | 36.9 | 46.9 | 43.8 |
| Water | 0.2 | 0.4 | 0.4 |
| MECHANICAL PROPERTIES (DRY/WET) | | | |
| Tensile Strength (psi) | 2671/2264 | 5971/5811 | 4317/3510 |
| 100% Modulus (psi) | 356/356 | 746/655 | 200/313 |

TABLE 1-continued

| | UNSUBSTITUTED PRIOR ART POLYMER A | SUBSTITUTED POLYMERS | |
|---|---|---|---|
| | | Example 1 | Example 2 |
| Elongation (%) | 600/487 | 450/475 | 495/600 |
| Tear Resistance (lb/in) | 181/69 | 475/271 | 213/163 |
| Water Content (%) | 53.6 | 32.0 | 31.0 |

As will be noted, substitution with the polyoxypropylene glycol results in a decrease in water absorption. Even more unusual is the more than doubling of tensile strength in both the dry and swollen state of the Example 1 polymer compared with the unsubstituted prior art polymer, but with modulus only slightly down. The Example 2 polymer where more of the hard segments were replaced, exhibits still further improved tensile strength, but is softer than either the prior art polymer or the Example 1 polymer with higher elongation and acceptable tear resistance.

EXAMPLE 3

The foregoing procedure for preparing prior art hydrophilic polyurethane B was repeated except that NIAX® PPG 2025 polyoxypropylene glycol was included as part of the diol blend. This polymer was produced by mixing and melting together 11.2 parts of CARBOWAX 1450, 7.7 parts of CARBOWAX 1000, 4.6 parts of CARBOWAX 600, 3.1 parts of CARBOWAX 400, 7.4 parts of ethylene glycol and 0.4 parts of water. Into the resulting mixture was dispersed 19.9 parts of NIAX® PPG 2025 and 45.7 parts of Desmodur W. Next was added 0.2 parts of stannous octoate after which an exothermic reaction occurred. The resulting polyurethane was cured at 90° C. for 80 minutes and then granulated. Properties of the finished polymer and the prior art polyurethane B are listed in Table 2.

TABLE 2

| POLYMER PROPERTIES (DRY/WET) | Prior Art Polyurethane B | Polymer of Example 3 |
|---|---|---|
| Water Content (%) | 50.9 | 41.6 |
| Tensile (psi) | 2900/1980 | 3662/2931 |
| 100% Modulus (psi) | 655/545 | 842/646 |
| Elongation at Break (psi) | 700/520 | 416/400 |
| Tear Resistance (lb/in) | 295/87 | 253/211 |

As the date in Table 2 shows, the polymer of Example 3 containing $OCH_2CH(CH_3)$— and —$OC_2H_4$— units in the polymer backbone exhibits higher tensile strength in the dry and wet state compared with the prior art polyurethane having a polymer backbone formed only of —$OC_2H_4$— units. Especially noteworthy is the wet state tear resistance of the Example 3 polymer, being 211 lb/in. as compared with the prior art polymer of 87 lb/in.

Polymer Applications

EXAMPLE A

Denture Liner

The polymer of Example 1 is placed in a Carver press at 104.4° C. to 115.5° C. and 3,000 pounds pressure and formed into a sheet 1–1.2 mm thick. The polymer plate is coated on one side with a layer of GELVA ™ RA 788 adhesive (vinylacetate acrylic multipolymer adhesive, sold by Monsanto Company) using a doctor blade. Following the drying of the adhesive layer, the soft polymeric sheet is adapted to the gum-contacting surface of a full upper denture, pressed into place and the excess cut off with a scalpel. After swelling in water, the polymer further softens and owing to its water content, exhibits water spreading on its surface. Thus, the advantage of this type of denture liner is two-fold: the soft layer cushions the denture and prevents erosion of the gums, and the hydrophilic surface increases the adhesion.

The above procedure is carried out a second time substituting the polymer of Example 2 for that of Example 1, to obtain substantially the same results.

EXAMPLE B

Wound Dressing

The polymer of Example 1 is dissolved in chloroform as a 10% solids solution, and a film thereof 3 mil thick is cast on release paper. When the last remnants of the solvent evaporates, a polyurethane/polyacrylic hydrophilic adhesive (Tyndale Plains-Hunter Ltd., Ringoes, N.J.) is spread on top of the polymeric film, using a doctor blade. The finished film when used as a wound dressing composite has a good moisture vapor transmission rate and oxygen permeability.

The procedure aforesaid is repeated but using the polymer of Example 2, to obtain substantially the same results.

EXAMPLE C

Transdermal Patch

A film is prepared as in Example B, but to the solution is added 10% of indomethacin (1-(p-chlorobenzoyl)-5-methoxy-2-methyl-3-indolylacetic acid)—an anti-inflammatory and analgesic—based on the weight of the polymer used. A film cast with the hydrophilic adhesive, when tested as a transdermal patch on rats, releases indomethacin at an effective rate.

EXAMPLE D

Leachable Carrier

A film is cast from the polymer of Example 1 using a formulation containing 10% by weight of polymer and 1% sodium bicarbonate in a solvent blend of 60 parts ethyl alcohol, 10 parts isopropyl alcohol and 20 parts water. After the film is dried to constant weight, it is eluted in distilled water at 25° C. A good elution rate of the sodium bicarbonate from the film is observed.

The above procedure is repeated except for substitution of the polymer of Example 2 for that of Example 1, with substantially the same results.

EXAMPLE E

Controlled Antibiotic Release

A 10% solution of the polymer of Example 1 is prepared in chloroform. Commercial tablets of antibiotic are coated with the polymer solution. A high percentage of the drug present elutes at 37° C. in distilled water over 15 hours.

The procedure is repeated but substituting the polymer of Example 2 for that of Example 1, to obtain substantially the same results.

EXAMPLE F

Controlled Analgesic Release

Commercial aspirin tablets (325 mg/tablet, product of Bayer Company, division of Sterling Drugs, Inc.) are coated with the 10% solution of the polymer of Example 1 in chloroform. At 25° C., a good elution rate in distilled water is observed. This experiment when repeated with ground tablets placed in capsules prepared from the above-mentioned polymer solution by dipping on a Teflon ® mandrel, also results in a good elution rate.

The procedure aforesaid is repeated using the polymer of Example 2 in place of that Example 1, with substantially the same results.

EXAMPLE G

Veterinary Drug Delivery

Triple-Sulfa Boluses, a veterinary product of Pfizer Agricultural Division, New York, N.Y., containing 90 grains sulfamethazine, 90 grains sulfanilamide and 60 grains sulfathiazole each in 824 mg of electrolyte salts, is coated with a solution of 10% solids of the polymer Example 1 in 90% ethyl alcohol. While the uncoated boluses dissolve almost immediately, the coated boluses eluted a substantial proportion.

Similar results are obtained using the polymer of Example 2 in place of the polymer of Example 1.

EXAMPLE H

Insecticide Delivery

Seventy (70) parts of the polymer of Example 1 are dissolved with 16 parts of Baythroid TM FCR 1272 (Cyano(4-fluoro-3-§phenoxyphenyl)methyl-3-(2,2-dichloroethenyl)-2,2-dimethyl-cyclo-propanecarboxylate), manufactured by Bayer, Leverkusen, FRG, in 350 parts of methyl alcohol. The solution is sprayed on 475 parts of ground corn cobs and left to dry thoroughly. The coated granules are spread outdoors, using a spreader delivering 15.4 lbs/acre. The area, originally infested with ticks, is substantially free of ticks for a period of four weeks, despite heavy rainfall and high temperatures. Control spreading, using only the insecticide on the granules (no polymer) in the same concentration, is effective only for 24 hours in controlling the tick population.

The aforesaid procedure is repeated by substituting the polymer of Example 2 for that of Example 1, to obtain substantially the same results.

EXAMPLE I

Antifogging Agent

A solution is prepared from 4 parts of the polymer of Example 1, 0.09 parts of the leveling agent Silwet TM L-7604 organosilicone fluid, (manufactured by Union Carbide Silicones Division), 90 parts of ethyl alcohol and 5 parts of water. The solution is weighed into aerosol cans. After capping with the valve and dip tube assembly, the cans are filled with DYMEL ® 22 (fluorocarbon propellant, manufactured by E. I. DuPont and de Nemours) in a ratio of 40 parts solution, 25 parts propellant. Glass plates and mirrors are sprayed with this solution. The dried film prevents fogging of such coated objects, and will withstand several 15 minute cylces in the fog chamber without fogging. The same solution may also be used for saturating nonwoven pads, packaged in foil envelopes to prevent a loss of solvent.

The procedure aforesaid is repeated by substituting the polymer of Example 2 for that of Example 1, with substantially the same results.

EXAMPLE J

Coated Cathether

A latex Foley urinary catheter is dip-coated with a solution made from 3 parts of polymer from Example 1 and 97 parts of dichloroethane. After air drying, the dipping is repeated. The coating is cured at 80° C. for 5 minutes. While the uncoated latex has a coefficient of friction of 0.4 (as measured according to ASTM D-1894-75), the coated catheter has a coefficient of friction in fully hydrated state of 0.18.

The procedure aforesaid is repeated except for substitution of the polymer of Example 1, with substantially the same results.

EXAMPLE K

Cosmetic Film

A solution prepared from 7 parts of polymer from Example 1, 88 parts of 200 proof SDA ethyl alcohol and 5 parts of water is used as a wrinkle patch. When applied to the skin in the area of wrinkles, it dries to an invisible, nonshiny film, which partially fills and masks the wrinkles. Makeup or blush can be applied directly on the polymeric film. The film is removed by applying water and stripping, usually in one piece.

Substitution of the polymer of Example 2 for that of Example 1 gives substantially the same results.

EXAMPLE L

Deodorant Delivery

A solution prepared from 4 parts of polymer from Example 1, 0.2 parts of a suitable fragrance, 88 parts of SDA 200 proof alcohol and 5 parts of water is placed into aerosol cans. The cans are capped with the valve assemblies and filled with 25 parts of DYMEL 22 propellant to 30 parts of solution. The resulting spray is used as a deodorant. When sprayed on skin, the films prevent moisture transport in the liquid form, but do not prevent moisture vapor transmission. Thus, the subject remains "dry", with no visible sweat formation on the skin. Moreover, the hydrated film releases the fragrance slowly over a period of several hours.

The above procedure is repeated except for substitution of Example 2 for that of Example 1, with substantially the same results.

EXAMPLE M

Intravenous Feeding Catheter

The polymer of Example 1 was cut into thin strips and fed into a 1 inch Killian vented extruder and continuously extruded. The extrusion conditions are set as follows:

Zone 1: 265° F.
Zone 2: 380° F.
Zone 3: 275° F.
Die: Off
Speed: 18 rpm
Pressure: Very low—does not register on gauge
Amps: 3-5

The die is selected to give a thin-wall tubing of French 2 size.

Using the polymer of Example 2 in place of that of Example 1, the procedure is repeated, giving substantially the same results.

EXAMPLE N

Body Implant

The extrusion conditions of Example M are repeated except that a die is selected to give a rod having a diameter of 3.5 mm. The rod can be used as an implantable storage device for both human and veterinary drugs.

EXAMPLE O

Condom

A 100% by weight solution of the polymer of Example 2 was prepared by dissolving 10 parts of the polymer in 80 parts of ethyl alcohol and 10 parts of water. To this solution, 0.2 parts of nonylphenoxypoly (ethyleneoxy) ethanol nonionic surfactant (Sold as "IGEPAL CO 630" by GAF Corporation) were added.

Condoms were manufactured by dipping glass mandrels in the solution, letting dry on ambient air, and after three dips, curing at 60° C. for 30 minutes. The condoms were place in water and eluted at room temperature. 30 mg of IGEPAL CO 320 eluted in the first 10 minutes, and 20 mg in the next 10 minutes.

EXAMPLE P

Elution Rates of Cast Film

Film were cast from the polymer solution of Example 1. In this procedure 10% by weight (based on dry polymer) of high molecular weight standards were incorporated and films were cast. The dry films were eluted in distilled water over a period of 60 hours. The standards were Trypsin (MW 23,000) and Horseradish peroxydase (MW 42,000). The elution rates were as follows (% of original loading eluted):

| Time | 20 hours | 40 hours | 60 hours |
|---|---|---|---|
| Trypsin | 38% | 51% | 62% |
| Horseradish Peroxydase | 20% | 26% | 30% |

EXAMPLE Q

Elution of Coated Boluses

Triple-sulfa boluses, a veterinary product produced by Pfizer Agricultural Division, and containing sulfamethazine, sulfanilamide and sulfathiazole, are water soluble. When the bolus is placed in distilled water, it disintegrates in about 10 seconds and is fully dissolved in about 30 seconds. Sample boluses were coated with a 10% solution of the polymer of Example 1 in 90% ethanol, and the coating was air-dried and cured at 50° C. for 20 minutes to remove any traces of solvent. The coated boluses were placed in distilled water, mixed at room temperature, and the concentration of the sulfocompounds was monitored in the eluting water by UV for 6 days. 23% of the original concentration eluted in one day, 36% in three days and 54% in six days.

EXAMPLE R

Coated Capsule

The polymer of Example 2, 15 parts, was dissolved in dichloroethane. A capsule was made by dipping glass rod with blunt ends in the mixture until a thickness of 80 microns was reached. The capsule was filled with 100 mg of tetracycline and sealed with the polymer solution. The capsule was placed in a cell, through which distilled water was passed at a rate of 21.6 cc/hour. 72 mg of tetracycline eluted at a steady rate in 18 hours.

EXAMPLE S

Coated Capsule

An aspirin capsule, containing 100 mg of aspirin, was completely coated, using the polymer solution from Example R. The capsule was placed in a cell and 25.7 cc of distilled water per hour was passed through the cell. In 24 hours, 35 mg of aspirin eluted at a steady rate.

EXAMPLE T

Coated Capsule

Indomethacin, 212 mg, was charged into a capsule as in Example R. At a water flow of 24.7 cc/hour through the cell, 180 mg of indomethacin eluted at a steady rate in 17 hours.

EXAMPLE U

Fragrance Release Film

The polymer of Example 2 (8 parts) Poseidon fragance (10 parts manufactured by Fabrique De Laire, France), medical grade ethyl alcohol (75 parts) and water (8 parts) were dissolved and mixed together. A 2 mm thick film was cast from the mixture and once the solvent evaporated, was placed in a gentle air stream at ambient temperature and at 45-50% relative humidity. The loss of fragrance was monitored gravimetrically. In the first 10 days, 65% of the fragrance originally present in the film evaporated. During the second 10 days, 82% fragrance evaporated, and in the last 10 days, 94% of the fragrance evaporated. Film of these types can be used as room fresheners, pomanders, etc., and also as fragrance-releasing coatings on various objects.

I claim:

1. A hydrophilic, thermoplastic polyurethane polymer, of improved dimensional stability and mechanical strength, said polymer having an average molecular weight of from about 10,000 to about 200,000 and comprising the reaction product of:
   A. a diol blend comprising
      (i) from about 2 to about 15 parts by weight of an alkylene glycol selected from ethylene glycol and diethylene glycol,
      (ii) from about 10 to about 80 parts by weight of a polyoxyethylene glycol having an average molecular weight of from about 400 to about 20,000, and
      (iii) from about 10 to about 60 parts by weight of a polyoxypropylene glycol having an average molecular weight of from about 200 to about 2500;
   B. an organic diisocyanate, the ratio of NCO to OH being from about 0.95:1 to about 0.98:1; and
   C. water in an amount of no more than about 0.5 parts by weight, the sum of A, B and C being on a 100 parts by weight basis.

2. The polymer of claim 1 wherein the polyoxypropylene glycol has an average molecular weight of about 1025.

3. The polyurethane polymer of claim 1 wherein the diisocyanate is an aliphatic diisocyanate selected from methylene bis(cyclohexyl-4 isocyanate), trimethyl hexamethylene diisocyanate, isophorone diisocyanate and cyclohexyl diisocyanate.

4. The polyurethane polymer of claim 1 wherein the diisocyanate is methylene bis(cyclohexyl-4-isocyanate).

5. A carrier system comprising an active agent and as a carrier vehicle therefor, the hydrophilic polyurethane polymer of claim 1.

6. The carrier system of claim 5 wherein the same is a nonleachable carrier system.

7. The carrier system of claim 5 wherein the same is a leachable medium system.

8. The carrier system of claim 7 wherein the leachable carrier system is an aqueous medium, leachable carrier system.

9. The carrier system of claim 8 wherein the carrier system is disposed in a liquid medium.

10. The carrier system of claim 9 wherein the liquid medium is a body fluid.

11. The carrier system of claim 5 wherein the carrier system is disposed in a gaseous medium.

12. The carrier system of claim 11 wherein the gaseous medium is air.

13. The carrier system of claim 5 wherein the polymer carrying the active agent is in the shape of a film.

14. The carrier system of claim 5 wherein the polymer carrying the active agent is in the shape of a rod.

15. A bodily implant comprising the rod-shaped polymer of claim 14 and wherein the active agent is leachable in contact with bodily fluids.

16. The carrier system of claim 5 wherein the active agent is a drug for human or veterinary use.

17. The carrier system of claim 13 wherein the film is a wound or burn dressing.

18. The carrier system of claim 13 wherein the active agent is a fragrance.

19. The carrier system of claim 13 wherein the active agent is a deodorant or antiperspirant.

20. A water absorbent coating comprising the hydrophilic polyurethane polymer of claim 1.

21. A low friction, water absorbent coating comprising the hydrophilic polyurethane polymer of claim 1.

22. The coating of claim 20 wherein the same is an antifogging coating.

23. The coating of claim 20 wherein the same is adapted for application to a boat hull for reduced friction flow.

24. The coating of claim 20 wherein the same is adapted for application to the inside of a duct for reduced friction flow.

25. The coating of claim 20 wherein the same is adapted for application to a medical device.

26. The coating of claim 25 wherein the medical device is a body implant.

27. The coating of claim 25 wherein the medical device is a cannula.

28. The coating of claim 25 wherein the medical device is a catheter.

29. As an article of manufacture, a shaped, three-dimensional structure formed of the hydrophilic, polyurethane polymer of claim 1.

30. The article of manufacture as defined in claim 29 wherein the structure is a film.

31. The article of manufacture as defined in claim 30 wherein the film is in the form of a glove.

32. The article of manufacture as defined in claim 30 wherein the film is in the form of a denture liner.

33. The article of manufacture as defined in claim 30 wherein the film is in the form of a condom.

34. A film forming cosmetic composition for application as a wrinkle patch comprising a solution of the polymer of claim 1 in an evaporable solvent.

35. A deodorant delivery system for applying an odor-controlling, moisture vapor permeable, but water impermeable, film to the skin, comprising a film-forming solution of the polymer of claim 1 in an evaporative solvent, and means for delivering the film-forming solution to the desired skin area.

36. The deodorant delivery system as defined in claim 35 wherein the delivery means is an aerosol vessel.

37. The article of manufacture as defined in claim 29 wherein the structure is a contact lens.

38. The article of manufacture as defined in claim 29 wherein the structure is an extruded shape.

39. The article of manufacture as defined in claim 29 wherein the structure is a tube.

40. The article of manufacture as defined in claim 29 wherein the structure is in the form of a bead.

41. The article of manufacture as defined in claim 39 wherein the structure is an intravenous catheter.

42. The article of manufacture as defined in claim 39 wherein the structure is a cannula.

43. The article of manufacture as defined in claim 39 wherein the cannula is a feeding tube.

44. The article of manufacture as defined in claim 29 wherein the structure is an intrauterine device.

45. The article of manufacture as defined in claim 29 wherein the structure is a body implant.

* * * * *